United States Patent [19]

Fogt et al.

[11] Patent Number: 4,846,182

[45] Date of Patent: Jul. 11, 1989

[54] METHOD OF PREPARING A FLUID ABSORBENT QUANTITATIVE TEST DEVICE

[75] Inventors: Eric J. Fogt, Maple Grove; Marye S. Norenberg, Blaine; Darrel F. Untereker, Cedar; Arthur J. Coury, St. Paul, all of Minn.

[73] Assignee: Medtronic, Inc., Minneapolis, Minn.

[21] Appl. No.: 551,055

[22] Filed: Nov. 14, 1983

Related U.S. Application Data

[62] Division of Ser. No. 338,274, Jan. 11, 1982, Pat. No. 4,444,193.

[51] Int. Cl.⁴ ............... G01N 31/02; G01N 31/22
[52] U.S. Cl. ............... 128/632; 128/636; 128/760; 422/56; 422/58; 423/305; 423/595; 436/79; 436/125; 436/165; 502/208; 502/317
[58] Field of Search ............... 423/305, 595; 502/208, 502/317; 422/56, 58; 436/79, 125, 164, 165; 128/632, 636, 760

[56] References Cited

U.S. PATENT DOCUMENTS

| | | | |
|---|---|---|---|
| 745,843 | 12/1903 | Von Hoessle | 423/595 |
| 2,784,715 | 3/1957 | Kestler | 604/20 |
| 3,043,669 | 7/1962 | Charles | 422/58 |
| 3,200,063 | 8/1965 | Wilson | 502/317 |
| 3,267,142 | 8/1966 | Young | 502/317 |
| 3,447,904 | 6/1969 | Rupe | 422/57 |
| 3,492,216 | 1/1970 | Riseman et al. | 204/419 |
| 3,600,331 | 8/1971 | Ingwalson | 502/208 |
| 3,699,963 | 10/1972 | Zaffroni | 424/435 |
| 3,703,890 | 11/1972 | Saunders, Jr. | 128/743 |
| 3,794,910 | 2/1974 | Ninke et al. | 128/760 |
| 3,894,531 | 7/1975 | Saunders, Jr. | 128/743 |
| 3,918,433 | 11/1975 | Fuisz | 128/760 |
| 4,003,978 | 1/1977 | Shiraishi et al. | 502/317 |
| 4,032,624 | 6/1977 | Lecerf | 423/595 |
| 4,141,359 | 2/1979 | Jacobsen et al. | 604/200 |
| 4,163,039 | 7/1979 | Emrich | 422/58 |
| 4,190,060 | 2/1980 | Greenleaf et al. | 128/760 |
| 4,209,020 | 6/1980 | Nielsen | 128/641 |
| 4,230,105 | 10/1980 | Harwood | 128/156 |
| 4,250,878 | 2/1981 | Jacobsen et al. | 128/803 |
| 4,280,959 | 7/1981 | Parthasarathy et al. | 502/208 |
| 4,324,908 | 4/1982 | Grasselli et al. | 502/208 |
| 4,325,367 | 4/1982 | Tapper | 128/803 |
| 4,329,999 | 5/1982 | Phillips | 128/760 |
| 4,444,193 | 4/1984 | Fogt et al. | 436/79 |
| 4,454,094 | 6/1984 | Bjorling | 422/56 |

FOREIGN PATENT DOCUMENTS 1965195 7/1971 Fed. Rep. of Germany ...... 128/640

OTHER PUBLICATIONS

Gregg et al, "A New Screening Test for Cystic Fibrosis", *Pediatrics*, vol. 36, No. 5, Nov. 1965, pp. 700–703.

(List continued on next page.)

*Primary Examiner*—T. Tung
*Attorney, Agent, or Firm*—Vidas & Arrett

[57] ABSTRACT

Preparation of an absorbent quantitative test device in the form of a flat patch. When placed on the skin of a subject, the device collects a fixed volume of sweat. It is particularly intended to be used in screen testing for cystic fibrosis by measuring the chloride level in sweat and providing a visual indication when the level is in excess of a predetermined concentration. A fill tab indicator undergoes a color change when the fixed volume of sweat has been collected signifying completion of the test. The device includes two concentric circular reaction areas of chemically treated absorbent paper or the like. The sweat sample is introduced into the device at the center of the first or inner circular reaction area which contains a chemical composition capable of reacting with all chloride in the sweat sample below a predetermined concentration value to screen out that amount of chloride. A second or outer ring-shaped reaction area contains a chemical composition which indicates a color change for any chloride reaching it in excess of the predetermined concentration value. The color change in the outer ring-shaped portion thereby provides a quantitative indication of the pressure of a concentration of chloride in the subject's sweat in excess of the predetermined concentration level.

7 Claims, 1 Drawing Sheet

OTHER PUBLICATIONS

Evaluation of the 3M Patch Test for Cystic Fibrosis (10 pages).

Evaluation of 3M Patch Test for Cystic Fibrosis (3 pages).

Evaluation of 3M Patch Test for Cystic Fibrosis (4 pages).

Evaluation of 3M Patch Test Plan for Testing Cystic Fibrosis (6 pages).

One Page Paper Entitled: "Subject: Cost Analysis Associated with the Evaluation of 3M Patch Tests for Cystic Fibrosis".

Saltesmo paper Brochure (1964).

Knights, Jr. et al, "Simplified Screening Test for Cystic Fibrosis of the Pancreas", J.A.M.A., vol. 169, No. 12, 3/21/59, pp. 89–90.

Gluck, L., "A Patch Test for Chloride in Sweat as a Simple Screening Method for Detecting Cystic Fibrosis of the Pancrease", *Pediatrics*, Apr. 1959, pp. 731–737.

Brochure entitled, "Quantab TM Chloride Titrators", Oct. 4, 1979.

"Iontophoresis—A Major Advancement", *The Eye, Ear, Nose and Throat Monthly*, vol. 55, Feb. 1976.

"Painless Anesthesia", *Medical Electronics*, by Yvonne Baskin, Univ of Utah.

"Iontophoretic Local Anesthesia for Conjunctival Surgery", *Annals of Opthamology*, May 1978.

"Treatment of Orthopaedic Infections with Electrically Generated Silver Ions", *The Journal of Bone and Joint Surgery*, vol. 60-A, No. 7, Oct. 1978.

"Opinions and Comments", *Physical Therapy*, vol. 57, No. 10, Oct. 1977, pp. 1193–1194.

"Suggestion from the Field", re: Acetic Acid Iontophoresis for Calcium Deposits, *Physical Therapy*, vol. 57, No. 6, Jun. 1977, pp. 658–659.

"Iontophoresis", Excerpt from an Article in *The Journal of the New York State Society of Physiotherapists, Inc.*, Annual Issue, Jun. 1959.

Brochure–"Iontophoresis, The Non-Invasive Administration of Drugs", by Motion Control, Inc., Feb. 1979.

Paper entitled "D.C. (GALVANIC) Current", Unidentified as to source and date.

Paper entitled "Electro Diagnosis", dated 8/12/71, by Medco Products Co., Inc.

Article entitled, "An Improved Adhesive Patch for Long-Term Collection of Sweat", Biomat., Med. Dev., Art. Org., 8(1), 13–21 (1980).

METHOD OF PREPARING A FLUID ABSORBENT QUANTITATIVE TEST DEVICE

This is a division, of application Ser. No. 338,274, filed Jan. 11, 1982, now U.S. Pat. No. 4,444,193.

BACKGROUND OF THE INVENTION

Preparation of a test device designed to perform a quantitative test on a given volume of a fluid to provide a visual indication when a certain substance is present in the fluid in an amount in excess of a predetermined amount.

In its preferred embodiment, the test device of the invention is specifically directed to a flat absorbent test patch device used in the screening of persons for cystic fibrosis. Consequently, the invention although of general applicability is described herein with specific reference to its use in screen testing for cystic fibrosis.

A simple screening test is particularly needed for cystic fibrosis because of its high incidence in children. About 1 in 1000 to 1 in 1400 infants are born with cystic fibrosis. Those having cystic fibrosis exhibit high mortality. As recently as 1963 one-third of the deaths from cystic fibrosis occurred in the first year of life; two-thirds in the first five years. The prognosis has recently improved due to early therapy and mortality has decreased to less than five percent in the first year of life. A group half-life of over 20 years can be reasonably expected if treatment is early.

An abnormality which is used to identify persons having cystic fibrosis is the unusually high chloride concentration in their sweat. A sweat chloride concentration significantly greater than normal is constantly present in all persons suffering from this disease.

BRIEF SUMMARY OF THE INVENTION

The preparation of the device includes a first reaction area, preferably in the form of a circular, preferably flat, absorbent body contacted by a surrounding, preferably flat, body of absorbent material which provides a second reaction area. Preferably, the surrounding body is circular or ring-shaped, although it may be any other shape. The outer or perimeter edge of the circular first reaction area contacts the entire inner edge of the ring-shaped second reaction area. A third reaction area, preferably in the shape of a small absorbent tab or even a complete, surrounding, outer body which may be ring-shaped also or any other shape, contacts the outer diameter of the second reaction area body. The purpose of the tab or its equivalent is to signify when the device is saturated with a given volume of the fluid being absorbed for test.

The absorbent bodies are enclosed in a preferably flat, fluid-tight envelope which is transparent on at least one side at least in the outer reaction area and fill indication area. The opposite side contains an inlet opening aligned with the center of the first reaction area for the introduction of the test fluid, such as sweat, thereto. This side also preferably carries a fluid collector which directs fluid to the inlet opening.

By selecting absorbent bodies of known absorbency and sizing them properly, the deivce is constructed and arranged to absorb a predetermined fixed volume of test fluid, such as sweat, to be evaluated for its content of a substance, such as chloride, in excess of a predetermined amount.

The inner circle or first reaction area is impregnated with a predetermined amount of a reactant which is provided in an amount sufficient to react with all of the substance contained in the absorbed test fluid below a predetermined concentration value. The second reaction area or outer ring is also impregnated with a reactant which reacts with the substance in the test fluid also. However, since the fluid is introduced at the center of the first reaction area and must migrate radially therethrough before reaching the concentric ring or second reaction area, the composition in the first reaction area reacts with any substance in the fluid below the predetermined value first. Any substance in the fluid in excess of the predetermined value is free to react with the reactant in the second reaction area only upon migration of the fluid and substance thereto. The reactant in the second reaction area is selected to provide color change upon exposure to or reaction with the excess substance thus visually indicating the fact that substance in excess of the predetermined amount is present in the test fluid.

The tab or its equivalent contains a reactant sensitive to the fluid or a component thereof which undergoes a visual change in appearance upon its being reached by the migrating fluid to indicate that the first and second reaction areas are saturated with the fluid and a fixed volume thereof has been collected.

DETAILED DESCRIPTION OF THE PREFERRED EMBODIMENT

The preferred embodiment of the device is intended for use in screen testing of subjects for cystic fibrosis. It is constructed and arranged to absorb a 50 $\mu l$ test sample of sweat and to indicate the presence of chloride in the sweat in excess of a concentration of 45 mM by providing a suitable, visually apparent, color change in the outer ring of the device. It may be modified to absorb differing amounts of sweat or other test fluids and to provide visual indication of various excess amounts of chloride or other fluid-contained substances. It is particularly useful for aqueous fluids having a dissolved salt to be determined.

Figure 1:
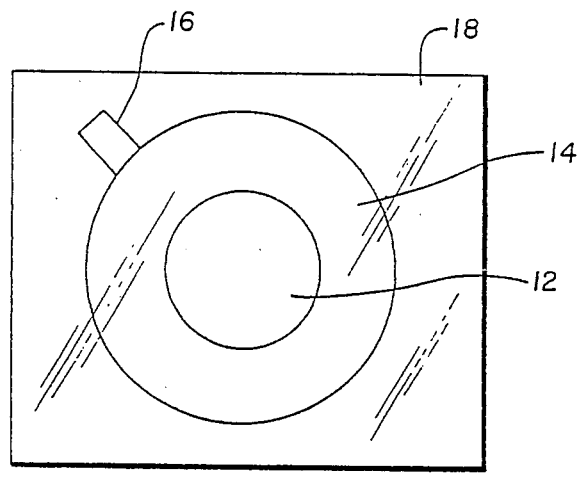
FIGS. 1 and 2 are top and bottom views, respectively, of a device according to the invention.
Figure 3:
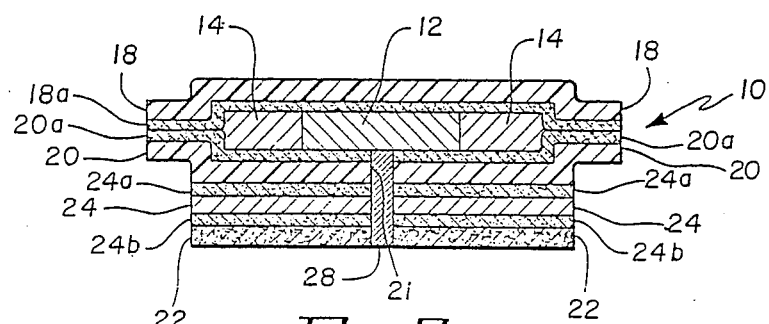
FIG. 3 is a schematic cross section taken through the center of the device shown in FIG. 1.

Referring now to the Figures, the device is comprised of an indicating layer generally indicated at 10 in FIG. 3. Indicating layer 10 includes inner circle 12, concentric ring 14 and tab 16 (seen in FIG. 1). Circle 12, ring 14 and tab 16 are of fluid absorbent material such as filter paper or chromotography paper and are preferably substantially flat. These bodies are assembled such that circle 12 lies inside ring 14 with the outer edge of circle 12 contacting the inner diameter of ring 14. Tab 16 contacts the outer diameter or edge of ring 14 as shown. Upon assembly of the three absorbent bodies into their operating relationship they are preferably subjected to pressure eg., 2600 lbs/sq inch to press them together. Tab 16 may be modified into various other shapes. For example, it may be a third concentric ring, ring segment or other shaped surrounded body. Generally, it may be any shape or form so long as it contacts the outer edge of ring 14 and provides a visually apparent color change when contacted by the fluid being absorbed or a constituent thereof.

The arrangement shown provides an indicating layer capable of absorbing a given volume of sweat depending on the size and weight of the absorbent paper selected and the overall size of the circular and ring-shaped bodies.

The various reaction areas may also be portions of a single body of absorbent material impregnated with a suitable pattern of reactant materials.

Indicating layer 10 is enclosed in a non-absorbent fluid-tight envelope comprised of an overlaying transparent layer 18 and an underlying backing layer 20. Layer 18 is transparent at least in a visually apparent portion of the second reaction area and of the fill indicator area. Layer 20 may be transparent also but not necessarily. A suitable and most preferred material for layers 18 and 20 is transparent adhesive plastic tape such as polyester tape obtained from Bel-Art Products, Pequannock, N.J. which markets a tape identified as "Lab Label Protection Tape". This tape has been found to be somewhat resistant to cold flow, non-absorbent and suitably transparent for use in forming the envelope in which indicating layer 10 is sealed between opposing adhesive surfaces of the tape 18a and 20a, respectively. Layer 20 is then provided with a small central opening 21 aligned with the center of circle 12 to provide an inlet opening for sweat to gain access to indicating layer 10.

Figure 2:
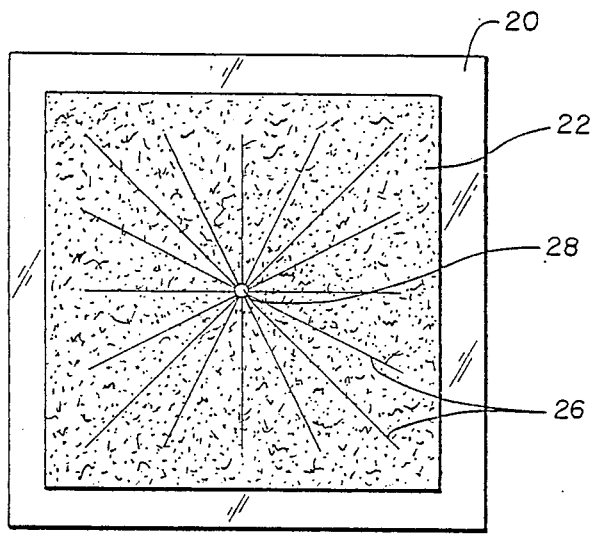

A sweat collector 22; preferably comprised of high density polyethylene non-woven sheet such as TYVEK ®, obtained from the Paper Manufacturing Company of Philadelphia, is then attached to layer 20. Preferably this is accomplished by means of a double backed adhesive plastic tape 24 (adhesive layers 24a and 24b) such as tape No. 1512 available from the 3M Company of St. Paul, Minn. Sweat collector 22 and plastic tape 24 also contain a central inlet opening aligned with the opening in layer 20 and with the center of circle 12. A piece of absorbent paper or the like is inserted into the inlet opening of the sweat collector as a wick-like plug 28 through which sweat enters the device to gain access to indicating layer 10. Sweat collector 22 also preferably includes a plurality of radiating indentations (best seen in FIG. 2) 26 which function to channel sweat to the inlet opening. These indentations may be formed by pressing or scribing the contact surface of the collector, i.e., the surface which is intended to contact the skin.

Inner circle 12 of indicating layer 10 is impregnated with a reactant so as to screen out all chloride in the sweat absorbed by the indicating layer below a predetermined concentration such as the aforementioned 45 mM. Outer ring 14 of indicating layer 10 is impregnated with a reactant so as to reflect the presence of chloride in excess of the screened concentration level by undergoing a color change to visually indicate the presence of the excess chloride. Tab 16 is also impregnated with a suitable composition to provide a visual indication that the indicating layer is saturated with the intended volume of sweat such as the aforementioned 50 μl amount. The fill tab indicator undergoes a color change only if the device absorbs the required volume of sweat. This serves as an indication that insufficient sweat has been generated and absorbed and likewise as an indicator that a sufficient amount of sweat has been generated and absorbed to complete the test.

The preferred absorbent medium for bodies 12, 14 and 16 is filter paper or chromatography paper. No. 20 chromatography paper from Whatman, Inc., Paper Division, Clifton, N.J., is most preferred.

Circles of desired size for inner circle 12 are preferably cut from sheets of such paper which have been impregnated with a controlled amount of silver phosphate. Preferably, the sheet is first impregnated with silver nitrate and dried. It is then impregnated with sodium phosphate to cause the formation of a silver phosphate precipitate in situ. These operations must be performed in subdued light. The silver phosphate thus formed has been found to be relatively immobile in the paper thus remaining fixed when sweat migrates through the circle. It gives the paper a yellow appearance.

Indicating rings 14 are cut to desired size from sheets of No. 20 chromatography paper which have been impregnated with silver chromate. The impregnation process is analogous to that described above in that the paper is first wetted with a silver nitrate solution, dried and then wetted with a potassium chromate solution to form silver chromate in situ.

Fill indicator tabs 16 are cut from the same sheets of paper which have been impregnated with silver nitrate in the same way.

Circle 12 (silver phosphate paper) is fitted inside brown ring 14 (silver chromate paper) and pressed together at 2600 lbs/sq. inch. This assembly is then placed on the adhesive side 18a of non-absorbent tape 18. Fill indicator tab 16 is placed on adhesive side 18a of tape 18 so that one edge touches the outer edge of ring 14. A hole or inlet opening, preferably approximately 0.04 inches, is punched in a second piece of tape i.e., layer 20 and this tape is placed over the paper bodies which are then sealed between the two tape layers with gentle pressing. The hole therein should be aligned so that it is in the center of circle 12. Channels 26 are formed in a radiating pattern in collector 22 which is preferably a piece of high density polyethylene non-woven fiber sheet. A hole, approximately 0.04 inches preferably, is punched in the center of sheet 22 and the sheet is attached to tape layer 20 with the holes aligned by means of the non-absorbent, double-backed adhesive tape 24 (which also has a 0.04 inch hole in its center). Wick-like plug 28 is formed from a plain piece of No. 20 chromatography paper which is punched to fit into the hole in the polyethylene sheet 22 and inserted therein as indicated in FIG. 3.

The operation of the device is as follows. Sweating is induced in a subject by any of a variety of methods. For example, sweat inducing drugs may be infused by iontophoresis techniques. After such a procedure, the skin area is cleaned with distilled water and dried. The test device is then taped over this cleaned area with the collector side of the device next to the skin. As sweat is generated the collector channels direct it towards the inlet opening where it enters the device by passing through the plug. The sweat enters the device at the center of inner circle 12. It radially diffuses through this first reaction area. Chloride in the diffusing sweat reacts with the impregnated silver phosphate in circle 12 as shown in reaction (1).

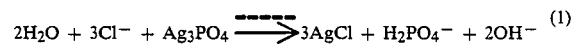
$$2H_2O + 3Cl^- + Ag_3PO_4 \longrightarrow 3AgCl + H_2PO_4^- + 2OH^- \quad (1)$$

As already indicated, sufficient silver phosphate has been impregnated in circle 12 so as to complex all chloride in the absorbed sweat sample below a predetermined concentration such as the aforementioned 45 mM value.

The sweat sample continues to radially diffuse outwardly and it enters ring 14. Any excess chloride i.e., chloride not reacted with the silver phosphate in circle 12, then reacts with the impregnated silver chromate in ring 14 as shown in reaction (2).

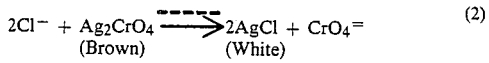
$$2Cl^- + Ag_2CrO_4 \longrightarrow 2AgCl + CrO_4^= \quad (2)$$
$$\text{(Brown)} \qquad \text{(White)}$$

Consequently, any chloride above the predetermined concentration is indicated visually by the appearance of a white area in ring 14.

Ring 14 preferably contains silver chromate formed in situ plus a slight excess amount of potassium chromate as shown in the Example below. As the sweat sample continues to diffuse outwardly in ring 14 it carries some of the soluble potassium chromate with it. When fill tab 16 is contacted by the sweat sample now containing the soluble chromate the following reaction takes place (3).

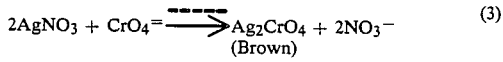
$$2AgNO_3 + CrO_4^= \longrightarrow Ag_2CrO_4 + 2NO_3^- \quad (3)$$
$$\text{(Brown)}$$

The tab turning brown indicates that sufficient sweat has been collected to saturate indicating layer 10 and that the test is complete.

EXAMPLE

A test patch capable of holding a 50 μl sweat sample and producing a color change in the indicating layer at 45 mM level of chloride concentration should have the following characteristics:

(1) inner circle 12—½ inch diameter impregnated with $1.7 \times 10^{-6}$ moles of silver phosphate (2) indicating ring 14—1 inch OD/one half inch ID, impregnated with about $2.2 \times 10^{-6}$ moles of silver chromate and $4 \times 10^{-7}$ moles of potassium chromate. The excess chromate is used to produce the color change in fill tabe 16 when the device is completely filled with fluid.

(3) Fill tab 16—⅛ inch by ¼ inch impregnated with $1.2 \times 10^{-7}$ moles of silver nitrate.
(Paper used throughout—Whatman No. 20 chromatography grade, thickness 0.165)

The amount of silver in circle 12 is slightly less than the amount required to complex all of the chloride in 50 μl of a 45 mM sample. The reason for this is that the last of the sweat sample to enter the test patch at inner circle 12 does not diffuse out to ring 14 and is therefore not involved in the reaction.

For cystic fibrosis application silver dichromate may also be used as the screening composition in ring 14. Cuprous chloride and chromic chloride may be used as color indicators for fill tabs 16. Other reactants are also considered to be within the scope of this invention and will be determined for any specific test fluid.

The following procedure has been found to be useful in impregnating the paper with a reproducible and evenly distributed amount of reactant.

A piece of dry bulk paper of known weight and size is saturated with water, placed between two sheets of 5 mil plastic sheet (e.g., Teflon) and passed through the rollers of a pasta maker to remove excess water. The bulk paper is immediately reweighed and from the difference in weight (wet-dry) the impregnation volume can be calculated. Using a #1. setting on the pasta maker, the procedure has been found to yield an average impregnation amount of 39 μl/in²±1 μl/in². It was noted that the speed one used in rotating the rollers has an effect on impregnation amounts. If the speed is slow more liquid is squeezed out of the paper. If it is fast, less liquid is squeezed out and the resulting impregnation volume is higher. A uniform rotational speed should be selected and used throughout.

Once the impregnation volume of the paper is determined, the concentration of the various impregnation solutions can be determined for any given situation.

Two important volumes must be known in order to construct this test patch. The first is the impregnation volume of the paper. This is a volume of impregnation solutions per square inch that the paper will hold. It must be experimentally determined using whatever impregnation procedure is developed, such as the method using pasta rollers described above. For Whatman #20 paper the impregnation volume was found to be 39±1 μl per square inch under the condition described here. Once this volume is known the concentration of chemicals needed to impregnate the bulk paper can easily be determined. The second volume of interest is the volume of test fluid the test patch will absorb during the screening test. It should be noted that this volume may be quite different from the impregnation volume. The absorption volume must be determined for the patch as constructed, i.e., with the specific kind of paper and the pressing conditions used during construction. For the test patch of the preferred embodiment of the invention the absorption volume was found to be 64±3 μl per square inch. It must be remembered that a volume of solution equal to that absorbed by inner circle 12 will never migrate to outer ring 14 during the test. Therefore, the calculation of the amount of silver phosphate needed to be impregnated into inner circle 12 depends only upon the size of outer ring 14. Thus, the volume of impregnation chemicals are calculated from the absorption volume and the size of the outer ring. It turns out that $1.7 \times 10^{-6}$ moles of chloride must be screened out in inner ½ inch circle 12 in the preferred embodiment described in the above Example. The impregnation volume for a ½ inch diameter circle is equal to 39 μl/sq. inch × 0.20 sq. inch (circle area) or 7.8 μl. This volume of solution must contain the required amount of silver for screening out the chloride or $1.7 \times 10^{-6}$ moles. The concentration of the $AgNO_3$ impregnating solution is, therefore, $1.7 \times 10^{-6}$ moles divided by 7.8 μl or 0.22M. The $AgNO_3$ is reacted with $Na_2HPO_4$ to provide the fixed silver phosphate reactant. A 0.21M $AgNO_3$ solution requires a 0.07M $Na_2HPO_4$ solution for stoichiometric formation of silver phosphate.

The preferred embodiment of the invention uses a test patch including an inner circle of ½ inch diameter and an outer ring about it bringing the total area to one inch. The inner circle must be impregnated with a specific amount of a certain concentration of $AgNO_3$. This is necessary so that the $Ag_3PO_4$ can be formed in the inner circle in a predetermined amount which will screen out 45 mM of chloride (or whatever predetermined amount is desired) in a given volume of sweat, such as 50 μl.

Outer ring 14 is used only as an indicating layer for excess chloride and the specific concentration of $Ag_2CrO_4$ is not critical. However, it has been determined that lower concentrations of $Ag_2CrO_4$ produce a more desirable result due to the fact that any excess chloride will produce a more significant visual change. Specifically, if one uses a high concentration of $Ag_2CrO_4$, when the excess chloride enters outer ring 14 there is so must silver ion in close proximity to inner circle 12 that all AgCl formation occurs in the area of the outer ring which is in very close proximity to the inner circle. By lowering the silver chromate concentration somewhat in the outer ring, the chloride can migrate further into it to provide an enlarged area of reaction and hence an enlarged visual indication of excess chloride. For example, one may preferably use 0.10M $AgNO_3$ and 0.07M $K_2CrO_4$ solutions to impregnate the outer ring for the most preferred embodiment of the invention.

For other applications, varying reactants may be used in the indicating layer. Various materials for the indicating layer per se and the sealing envelope as well as the collector and plug may also be used. The embodiments described herein has been by way of illustration only.

What is claimed is:

1. A method of preparing a quantitative testing device designed to provide a visual indication of a quantity of a substance in excess of a predetermined amount in a given volume of a test fluid, particularly wherein the test is for determining amounts of sodium chloride in human sweat in excess of a predetermined amount, comprising the steps:

forming a first reaction area comprised of an absorbent medium of predetermined absorbency;

impregnating the first reaction area absorbent medium with a predetermined quantity of silver phosphate for reaction with sodium chloride in the sweat;

forming a second reaction area of an absorbent medium;

impregnating the second reaction area absorbent medium with a quantity of silver chromate or dichromate for reaction with sodium chloride in the sweat which reaches the second area thereby providing a visual indication of the presence of sodium chloride in the second area, and passing the sweat test fluid through the first reaction area and then into the second reaction area.

2. The method of claim 1 wherein the silver phosphate and silver chromate or dichromate are respectively formed and precipitated in situ in the absorbent media.

3. The method of claim 2 wherein the respective formation and precipitation is with sodium phosphate/silver nitrate and potassium chromate/silver nitrate.

4. The method of claim 2 wherein the in situ silver phosphate is formed by:
    wetting the absorbent medium with silver nitrate solution;
    drying the medium, and
    reacting the silver nitrate in the medium with sodium phosphate solution.

5. The method of claim 2 wherein the in situ silver chromate or dichromate is formed by:
    wetting the absorbent medium with silver nitrate solution;
    drying the medium, and
    reacting the silver nitrate in the medium with a quantity of potassium chromate or dichromate solution slightly in excess of the silver nitrate.

6. The method of claim 3 wherein silver dichromate is formed in situ by use of potassium dichromate.

7. A method of preparing a quantitative testing device designed to provide a visual indication of a quantity of sodium chloride in human sweat in excess of a predetermined amount in a given volume of sweat, the method comprising the steps:

forming a first reaction area comprised of an absorbent medium of predetermined absorbency;

impregnating the first reaction area absorbent medium with a predetermined quantity of first reactant selected to react with the substance in the fluid and wherein the first reactant comprises silver phosphate;

forming a second reaction area of an absorbent medium;

impregnating the second reaction area absorbent medium with a second reactant selected to react with the substance and provide a visual indication of the reaction and wherein the second reactant comprises silver chromate;

arranging the first and second reaction areas such that the test fluid must be passed through the first reaction area in order to reach the second reaction area, and wherein a third reaction area is included for receiving fluid which passes through the second reaction area and the second reaction area is of a predetermined absorbency; and further wherein the third area contains silver nitrate and the second reaction area contains an amount of potassium chromate which is carried by any excess fluid to the third reaction area for reaction with the silver nitrate therein.

* * * * *

UNITED STATES PATENT AND TRADEMARK OFFICE
CERTIFICATE OF CORRECTION

PATENT NO. : 4,846,182
DATED : July 11, 1989
INVENTOR(S) : FOGT, ERIC J. ET AL

It is certified that error appears in the above-identified patent and that said Letters Patent is hereby corrected as shown below:

Col. 1, line 64, delete "deivce" and insert - device -

Col. 3, line 3, delete "abosrbent" and insert - absorbent -

Col. 5, line 41, delete "tabe" and insert - tab -

Signed and Sealed this

Seventeenth Day of April, 1990

Attest:

HARRY F. MANBECK, JR.

*Attesting Officer*  *Commissioner of Patents and Trademarks*